United States Patent [19]

Branemark

[11] Patent Number: 5,133,762
[45] Date of Patent: Jul. 28, 1992

[54] SYSTEM FOR RESTRUCTURING WRIST JOINTS

[76] Inventor: Per-Ingvar Branemark, Andergatan 3, S-431 69 Molndal, Sweden

[21] Appl. No.: 691,143

[22] Filed: Apr. 25, 1991

[30] Foreign Application Priority Data

Apr. 26, 1990 [SE] Sweden .................. 9001521

[51] Int. Cl.$^5$ .............................................. A61F 2/42
[52] U.S. Cl. ...................................... 623/21; 623/18; 623/20; 623/16
[58] Field of Search .................. 623/21, 18, 17, 19

[56] References Cited

U.S. PATENT DOCUMENTS

| | | | |
|---|---|---|---|
| 4,003,096 | 1/1977 | Frey | 128/92 |
| 4,040,130 | 8/1977 | Laure | 1/24 |
| 4,055,862 | 11/1977 | Farling | 623/20 |
| 4,946,378 | 8/1990 | Hirayama et al. | 623/17 |
| 5,011,497 | 4/1991 | Perssons et al. | 623/18 |

FOREIGN PATENT DOCUMENTS

1412376 11/1975 United Kingdom .................. 1/100

*Primary Examiner*—Randall L. Green
*Assistant Examiner*—Dinh X. Nguyen
*Attorney, Agent, or Firm*—Ostrolenk, Faber, Gerb & Soffen

[57] ABSTRACT

A system for reconstructing joints, particularly wrist joints. The system comprises three main components. A first main component (1) with a front plate (2) to hold an anchoring member screwable into the bone tissue close to the joint, and at least one pin (5) partially hollow, protruding from and the front plate (2) towards the bone tissue. A second main component (14) with a front plate (15) to hold an anchoring member (17) applied in the bone tissue close to the joint, and at least one pin (20) partially hollow, protruding from the front plate (15) towards the bone tissue. A third main component (33) comprising an artificial joint mechanism in the form of an elastomeric material which, by means of pins protruding from the joint mechanism, is intended to be positioned and secured in said hollow pins and/or attachment screws in the front plates (2; 15) of said first and second main components (1; 14) facing each other.

8 Claims, 3 Drawing Sheets

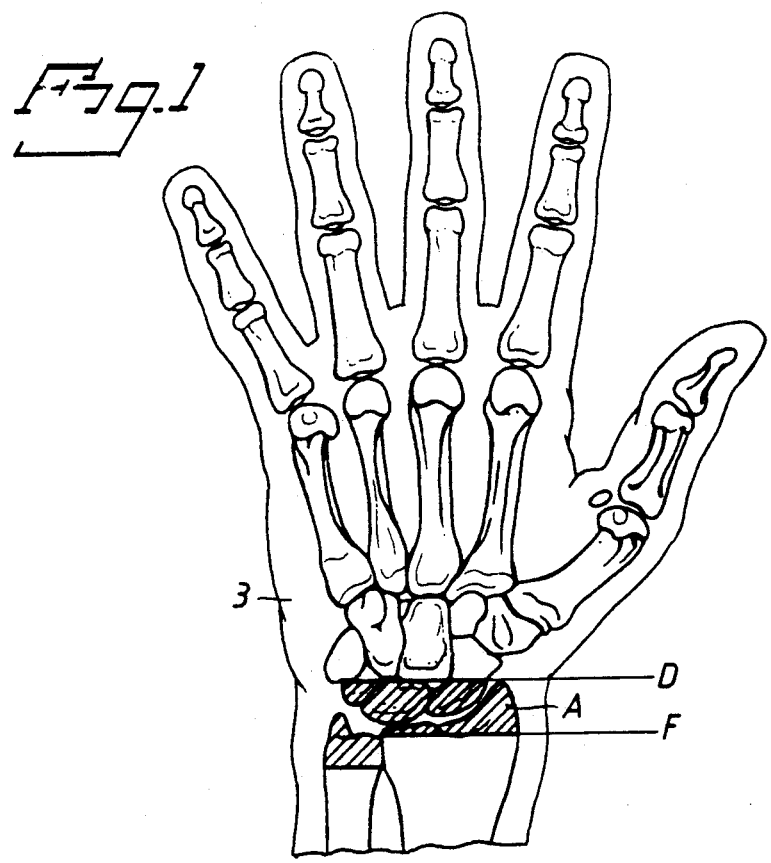
Fig.1
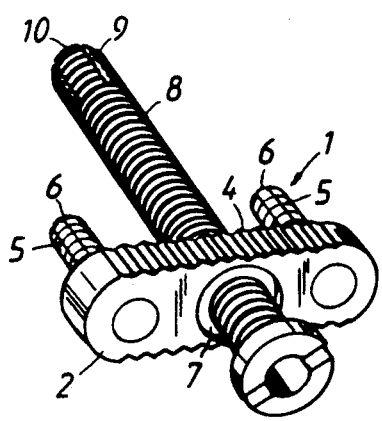
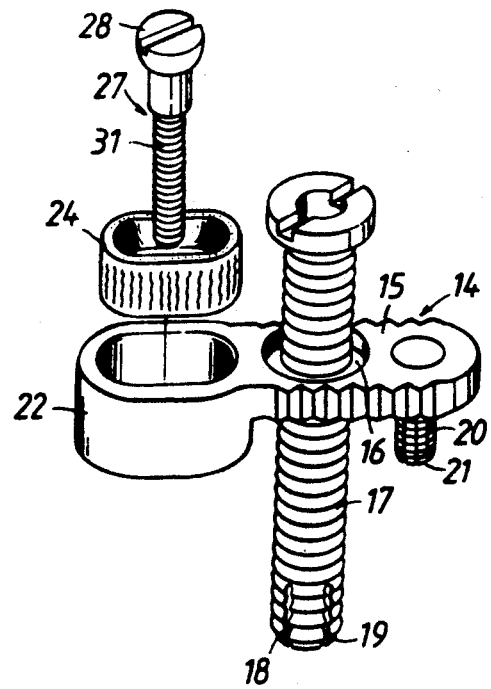
Fig.2

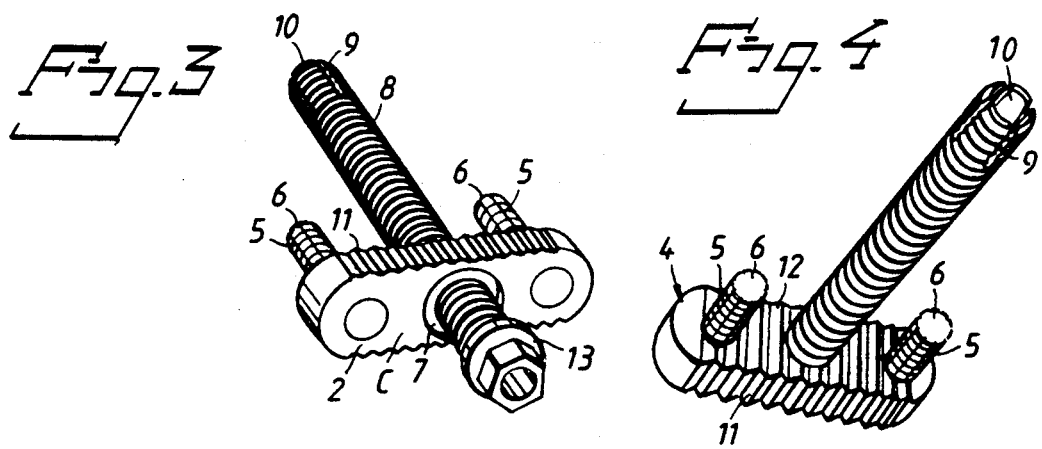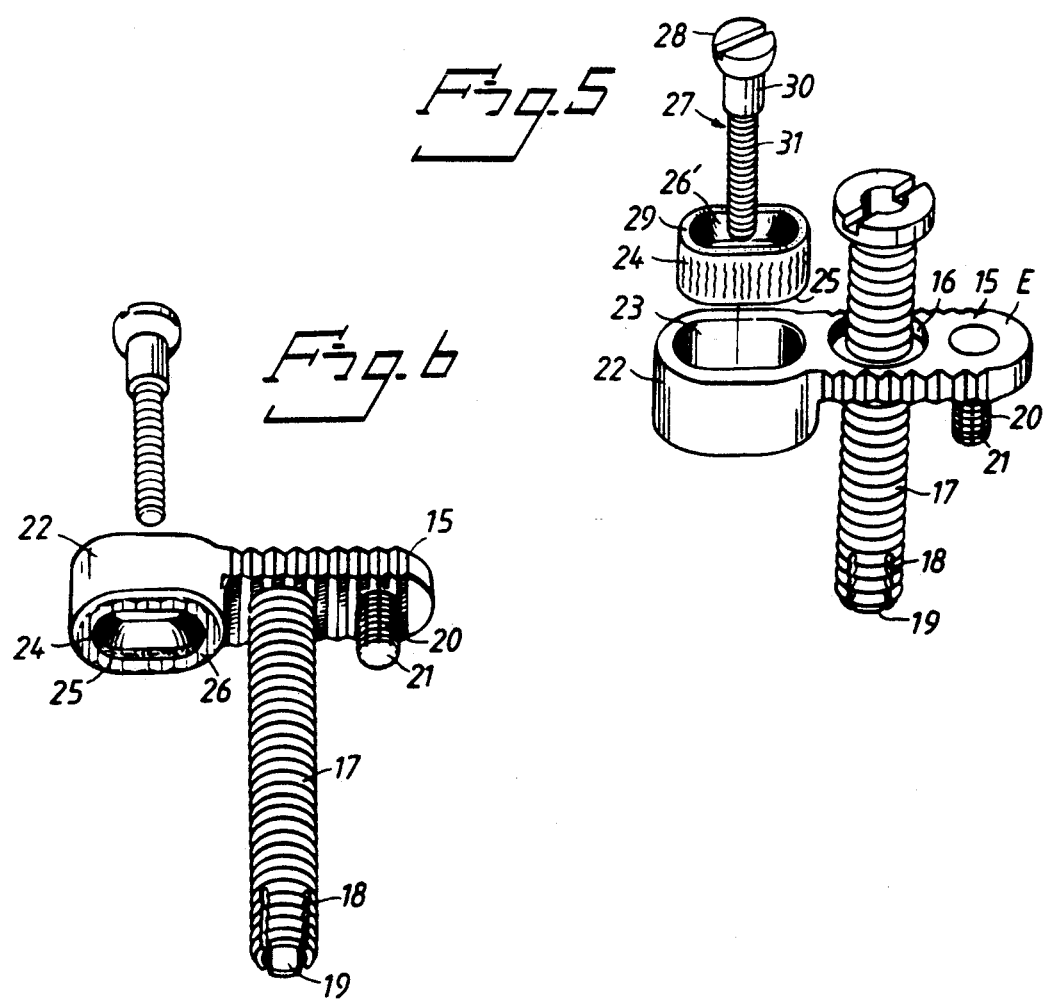

SYSTEM FOR RESTRUCTURING WRIST JOINTS

BACKGROUND OF THE INVENTION

The present invention relates to a system for reconstructing joints, particularly wrist joints.

Reconstruction systems for wrists known hitherto are few and not very efficient. The Swanson prosthesis is most usual in this respect. It consists of a guide body of elastomeric material with spikes protruding from it to be secured in spaces provided in respective marrow cavities.

The constant friction between these securing spikes and the adjacent tissue results in damage and consequent risk of inflammation and tendency to loosen. Furthermore, the elastomeric material used has not proven to be sufficiently wear-resistant. However, the most serious drawback of these known joint prostheses is that they only partially solve the problem. They may permit "normal" bending of the wrist but do not allow the wrist to turn at the same time.

Another recent example of a system for reconstructing the distal radial ulna joint does not hands. See U.S. application Ser. No. 630,518, filed Dec. 20, 1990, now abandoned. Additionally, that system concerns only rotation movement at the wrists, i.e. pronation and supination by a pivot joint between the ulna and the ulnar notch of the radius. Bending motion is not addressed in that system.

SUMMARY OF THE INVENTION

It has now surprisingly been found that these drawbacks of known joint replacements can be eliminated by means of the invention which permits "normal" bending of the wrist and also allows the wrist to turn as necessary, thereby providing a joint replacement with substantially the same functioning as a normal joint.

Other objects and features of the invention are described in the following with reference to an embodiment shown in the accompanying drawings.

BRIEF DESCRIPTION OF THE DRAWINGS

FIG. 1 shows the structure of a hand with a normal wrist,

FIG. 2 is a perspective view of the various components included in the system according to the invention for reconstructing a wrist, FIGS. 3 and 4 show different direction perspective views of the first main component of the system according to the invention, FIGS. 5 and 6 show different perspective views of the second main component of the system according to the invention.

DESCRIPTION OF A PREFERRED EMBODIMENT

Figure 7:
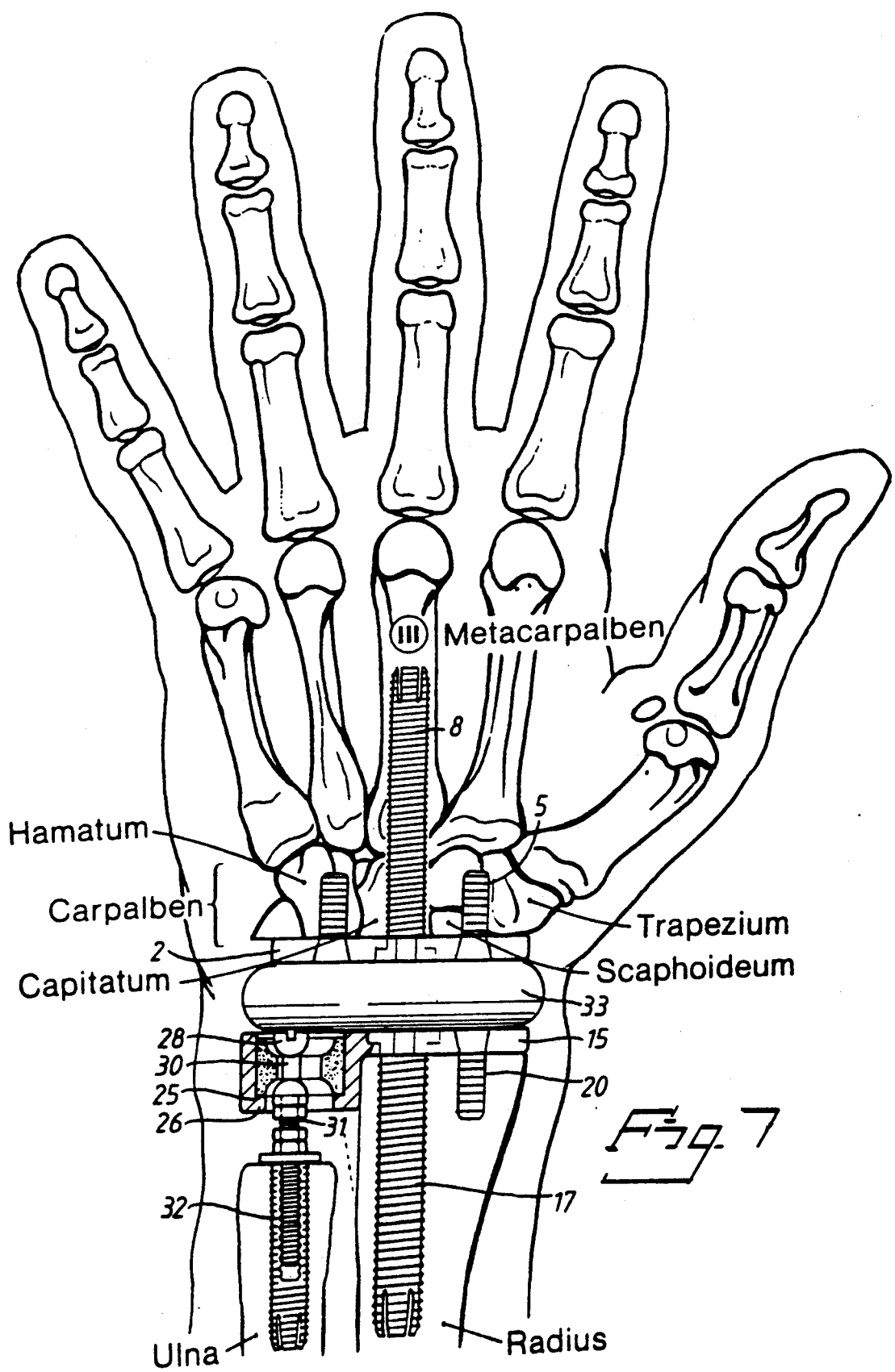
FIG. 7 illustrates the system applied in accordance with the invention.

FIG. 1 shows the structure of a normal wrist. When reconstructing a wrist by means of the system according to the present invention, the parts shown in the shaded sections A in FIG. 1 are surgically removed and are replaced by an artificial joint described below.

A diagrammatic sketch of the system according to the invention is shown in FIG. 2 where a first main component is designated 1. This first main component comprises a front plate 2. The hidden (hidden from view) side of the plate, when applied to the wrist, is directed toward the palm of the hand 3. The plate 2 is provided with two at least partially hollow pins 5 which are spaced apart and which, protrude toward the palm 3. The ends 6 of the pins 5 are closed. Between the pins 5 there is an aperture 7 for receiving a screw-like anchoring member 8. That anchoring member is in known manner partially hollow and is provided with slits 9 in the form of cutting edges in its open end 10.

Further details of the first main component of the system are revealed in FIGS. 3 and 4.

The first main component is either manufactured entirely from biocompatible material, or at least it has a surface coating of such material, e.g. titanium. The front plate 2 is suitably provided along its opposite long side edges with grooves 11 which run in the direction of insertion in order to improve the fusion, i.e. osseointegration, of the plate into the bone tissue. The surface of the upper side 4 of the front plate 2 as seen in FIG. 4 is also suitably irregular, and that surface is provided with grooves 12, for instance. The aperture 7 in the front plate 2 is recessed to hold the upper flange 13 of the anchoring member 8.

The second main component 14 in the system is shown in detail in FIGS. 5, 6 and 7. It projects back into the arm.

The second main component also comprises a front plate 15 with an opening 16 for a screw-like anchoring member 17 which, like the anchoring member 8 in the first main component 1, is partially hollow and has slits 18 which form cutting edges into its open end 19.

A hollow pin 20 with a closed end 21 protrudes from the plate 15 and is on one lateral side of the opening 16. At the other lateral side of the opening 16 the front plate 15 continues into a sleeve shaped guide body 22 which protrudes from the front plate 15 in the same direction as the pin 20. The guide body 22 is provided with a substantially oval borehole 23 through it designed to receive a substantially oval insert 24. The base 25 of the insert 24 is at least partially in contact with an inwardly protruding end flange 26 of the guide body 22. The insert 24 is provided with a slot-shaped longitudinal guide 26' and is designed to receive a control member 27 with head 28 that is arranged to abut against the upper limit 29 of the slot so that the smooth section 30 adjacent the head 28 of the control member 27 is principally located inside the insert 24.

The control member 27 is also provided with a lower, threaded portion 31 which is to be screwed permanently into a fixture 32 previously arranged in the relevant bone tissue (ulna).

All parts of the second main component, except for the insert 24, are made of a biocompatible material, preferably titanium. The insert 24, on the other hand, is made of a plastic material, suitable high density polyethylene.

The system according to the present invention also includes a third main component 33 in the form of a joint mechanism which may consist, for instance, of a resilient cushion of silicon plastic. The cushion is intended for placement between the front plates 2 and 15 of the first and second main components 1 and 14, respectively. The cushion is secured in position by pins that protrude from the cushion 33 and are inserted into both hollow pins 5 in the front plate 2 and into the pin 20 and also into the upper, hollow part of the attachment screw 17 in the second main component.

The system according to the invention is applied in the following manner.

First, the damaged or defective natural part of the wrist is removed, which includes the shaded sections A in FIG. 1. A titanium fixture 32 is then applied in known manner in the ulna, and it is ready to receive the screw thread 31 on the control member 27.

The front plate 2 of the first main component, after necessary preparation, is applied so that the substantially flat front surface C of the plate 2 lies in a plane with the line D in FIG. 1.

The front plate 2 is secured in position by screwing the attachment screw 8 into the metacarpel bone III (FIG. 7).

After the requisite preparation, the front plate 15 of the second main component 14 is then applied so that its flat side E is located in substantially the same plane as the line F in FIG. 1. The front plate 15 is then secured in position by screwing the attachment screw 17 into the radius. Thereafter, the insert 24 is placed in the guide body 22, whereupon the control member 27 is passed from above through the insert 24, and the lower, threaded portion 31 of the member 27 is screwed into the fixture 32. The extent to which the threaded portion 31 is screwed in may be varied by means of stop members in the form of nuts or the like. Finally, the joint mechanism 33 is arranged between the front plates and is secured as described above.

The system applied in the manner described gives a joint function comparable to a normal joint. The main bending movement of the wrist is achieved through the joint mechanism 33, while the desired rotation of the wrist (i.e. rotation of the radius about the ulna) is also achieved via the arrangement of the control member 27, which enables a rotary movement of 35 90 degrees.

The invention is of course not limited to the embodiments shown in the drawing but can be varied in many ways.

Although the present invention has been described in connection with a preferred embodiment thereof, many other variations and modifications will now become apparent to those skilled in the art. It is preferred, therefore, that the present invention be limited not by the specific disclosure herein, but only by the appended claims.

What is claimed:

1. A system for reconstructing a wrist joint comprising:
   a first main component comprising a first front plate with an outward facing side for facing toward the hand and an opposite inward facing side, a first anchoring pin supported in the first front plate, protruding from the outward facing side of the front plate and for extending toward a bone on the outward facing side of the first front plate;
   a second main component comprising a second front plate having a second inward facing side for facing away from the hand and an opposite second outward facing side, a second anchoring pin supported on the second front plate and for extending into the bone at the second inward facing side of the second plate;
   a third main component comprised of elastomeric material and disposed between the inward facing side of the first front plate and the second outward facing side of the second front plate, and means on the first and second plates and on the third component for securing them together, the elastomeric material of the third component being deformable for permitting the hand to move at the wrist, and further comprising guide means disposed on the second component and a control element extending from the guide means for extending into the ulna bone of the wrist, the guide means being connected to the second front plate of the second component, and the guide means being so shaped and positioned as to permit rotary movement of the reconstructed wrist.

2. The system of claim 1, wherein the attachment of the third component to the first and second components comprises pins projecting from the third component into the first and second components.

3. The system of claim 1, wherein the second anchoring pin is intended to extend into the radius bone of the wrist.

4. The system of claim 1 wherein the guide means comprises the second front plate having a guide body with a slot shaped guide opening through it, the control element provided for extending into the ulna bone and securement therein and the control element located outside the guide body and the guide opening thereof, whereby the cooperation of the control element and the guide body enables movement of the hand at the wrist.

5. The system of claim 4 wherein the control element and the slot shaped guide opening are respectively so shaped that the control element is both rotatable and displaceable in both the lateral and vertical directions with respect to the slot shaped guide opening.

6. The system of claim 5 further comprising a sleeve like body of a polymer material inserted in the guide body and the slot shaped guide opening being defined in the sleeve like body.

7. The system of claim 6, wherein the sleeve like body is comprised of a polymer material.

8. The system of claim 7, wherein the first and second main components comprise titanium.

* * * * *